United States Patent [19]
Michael

[11] Patent Number: 6,162,406
[45] Date of Patent: Dec. 19, 2000

[54] ELECTRODELESS DISCHARGE SYSTEM FOR ULTRAVIOLET WATER PURIFICATION

[75] Inventor: Joseph Darryl Michael, Clifton Park, N.Y.

[73] Assignee: General Electric Company, Schenectady, N.Y.

[21] Appl. No.: 09/344,084

[22] Filed: Jun. 25, 1999

[51] Int. Cl.[7] .................................................... B01J 19/08
[52] U.S. Cl. ........................................................... 422/186.3
[58] Field of Search .................... 422/186.03, 186.07, 422/186.3

[56] References Cited

U.S. PATENT DOCUMENTS

| | | | |
|---|---|---|---|
| 4,156,652 | 5/1979 | Wiest | 250/527 |
| 4,273,660 | 6/1981 | Beitzel | 210/760 |
| 4,535,247 | 8/1985 | Kurtz | 250/436 |
| 4,694,179 | 9/1987 | Lew et al. | 422/186.3 |
| 4,769,131 | 9/1988 | Noll et al. | 210/86 |
| 5,326,539 | 7/1994 | Taylor | 422/186.07 |
| 5,382,878 | 1/1995 | Secen et al. | 315/248 |
| 5,760,547 | 6/1998 | Borowiec | 315/248 |
| 5,959,405 | 9/1999 | Soules et al. | 313/635 |

*Primary Examiner*—Kathryn Gorgos
*Assistant Examiner*—Thao Tran
*Attorney, Agent, or Firm*—Jill M. Breedlove; Douglas E. Stoner

[57] ABSTRACT

Water is disinfected by causing the water to flow around an electrodeless low pressure mercury discharge lamp having high ultraviolet transmission properties.

9 Claims, 4 Drawing Sheets

EXHAUST TUBE 14

ELECTRODELESS DISCHARGE SYSTEM FOR ULTRAVIOLET WATER PURIFICATION

BACKGROUND OF THE INVENTION

The present invention generally relates to systems for disinfecting water using irradiation, and in particular to use of ultraviolet radiation for disinfection of water.

Ultraviolet (UV) radiation has long been known to be an effective disinfectant for water. Prior art UV disinfection systems rely on the use of electroded linear low pressure discharge lamps that use mercury. These linear systems are very similar to standard fluorescent lamps in terms of operation, except that there are no phosphor coatings and the glass used (a hard glass, not quartz) usually transmits a substantial amount of the 254 nm radiation emitted from the mercury atom. These electroded systems have two typical modes of failure: 1) electrode failure and 2) solarization of the glass due to the UV flux.

It would be desirable to provide a UV water purification device having a longer-lived lamp and ballast, made of high quality quartz which does not degrade as rapidly as treated hard glass. It would be furthermore desirable that such a device have a compact design and operate at higher power and provide higher UV output.

BRIEF SUMMARY OF THE INVENTION

A low-pressure electrodeless lamp having high ultraviolet transmission properties is used for disinfection of water. The ultraviolet output is directed from the low pressure discharge into a quartz housing around the lamp, through which water is channeled. The housing may be cylindrical with the lamp being centered on the axis of the cylinder.

DETAILED DESCRIPTION OF THE INVENTION

Figure 1:
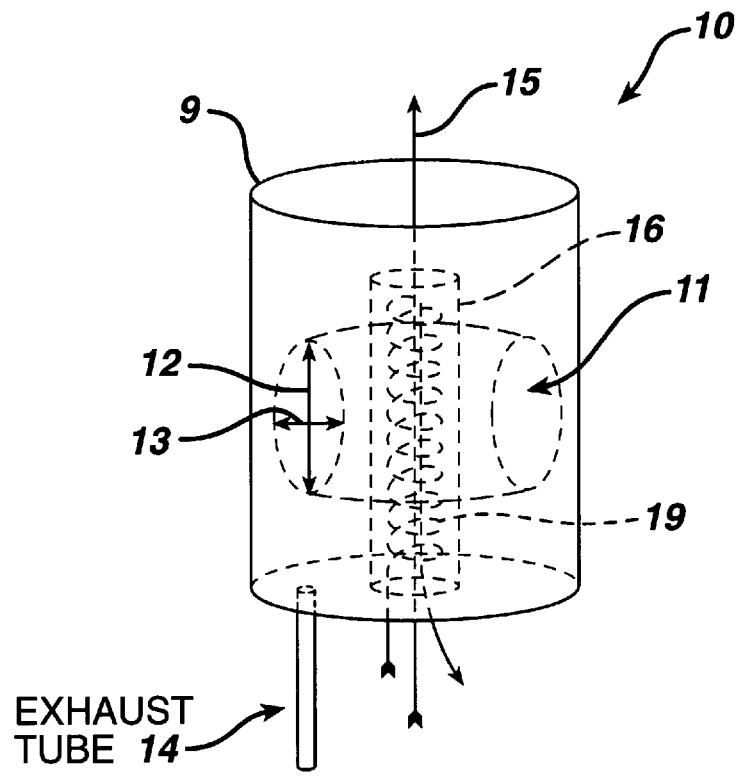
FIG. 1 is a perspective drawing of a lamp such as described herein useful for generating ultraviolet radiation and disinfecting water.

FIG. 1 illustrates an embodiment of an electrodeless fluorescent lamp 10 according to the present invention. Such an electrodeless fluorescent lamp may be manufactured using technology of a type employed to manufacture lamps such as those sold under the trademark GENURA of General Electric Company. Lamp 10 has an envelope 9 containing an ionizable, gaseous full. Envelope 9 is preferably made of quartz.

A suitable fill for the electrodeless fluorescent lamp of FIG. 1 comprises a mixture of a rare gas (e.g., krypton and/or argon) and mercury vapor and/or cadmium vapor. A re-entrant cavity 16 within the envelope 9 has an excitation coil 19 associated therewith, e.g., contained within the re-entrant cavity. Envelope 9 fits into one end of a lamp base assembly (not shown), such as an Edison type base, for example, for coupling to a radio frequency power supply.

In operation, current flows in excitation coil 19 as a result of excitation by the radio frequency power supply. As a result, a radio frequency magnetic field is established within envelope 9, in turn creating an electric field which ionizes and excites the gaseous fill contained therein, resulting in a UV discharge 11. A useful UV discharge is in the range up to about 400 nm, particularly at 254 nm. For the illustrated embodiment, the discharge body 11 is toroidal in shape.

By way of illustration, an exemplary compact design of electrodeless fluorescent lamp 10 of FIG. 1 has a 20W discharge, and the cross section of the toroidal discharge can be represented by an ellipse with a major axis 12 of about 23 mm and a minor axis 13 of approximately 13 mm. For this example, the major radius (measured from the center of the discharge 11 to the axis 15 running through the center of re-entrant cavity 16) of the discharge is at 18.75 mm. An exemplary outside diameter (OD) may be as large as 80 mm. A larger OD enables operation of the device without saturating UV output, but may increase the difficulty of manufacturing the lamp body. There is also shown in FIG. 1 an exhaust tube 14 used for filling the lamp during the manufacture thereof. In alternative embodiments, the exhaust tube may be situated at other positions in the lamp without effecting operation of the lamp as described herein.

For the example set forth hereinabove, simulations indicate that the main portion of the UV flux exits the lamp 10 from the discharge body 11 within a width (in the direction of the major axis 12) of 23 mm centered on the discharge body 11. For a lamp having an OD of 50 mm, for example, the total circumferential surface area is $\pi \times 50$ mm$\times 23$ mm=36 cm$^2$; and for a discharge of 20W, simulations show that the amount of 254 nm radiation directly impinging on this region is about 6W. This means that the UV flux, $\Gamma$, through this band is $\Gamma = 6W/36$ cm$^2 = 0.17$ W/cm$^2$.

Figure 2:
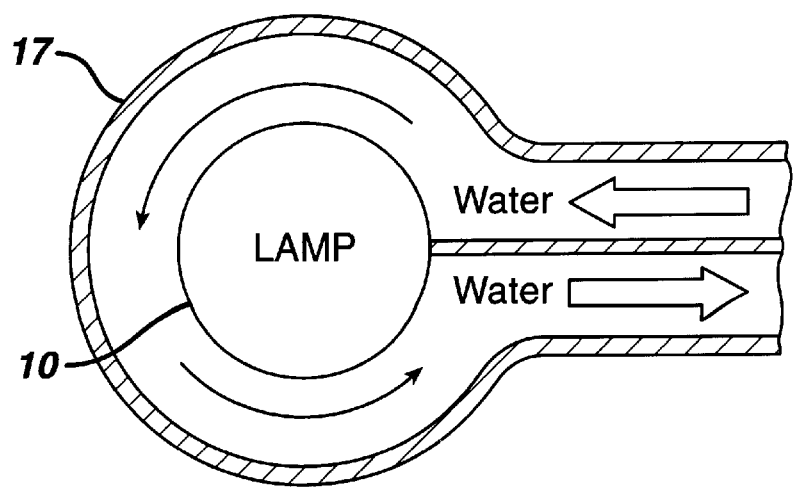
FIG. 2 is an overhead view of the lamp in FIG. 1 showing the flow of water around the lamp.
Figure 5:
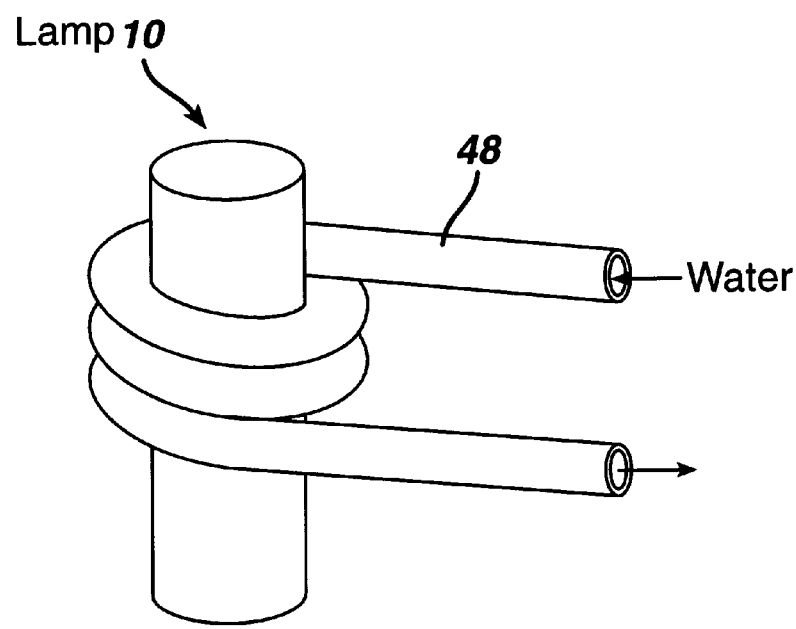
FIG. 5 is a perspective drawing of an embodiment of the invention having the flow of water channeled in a single tube wrapped three times around the lamp in a concentric loop configuration.
Figure 6:
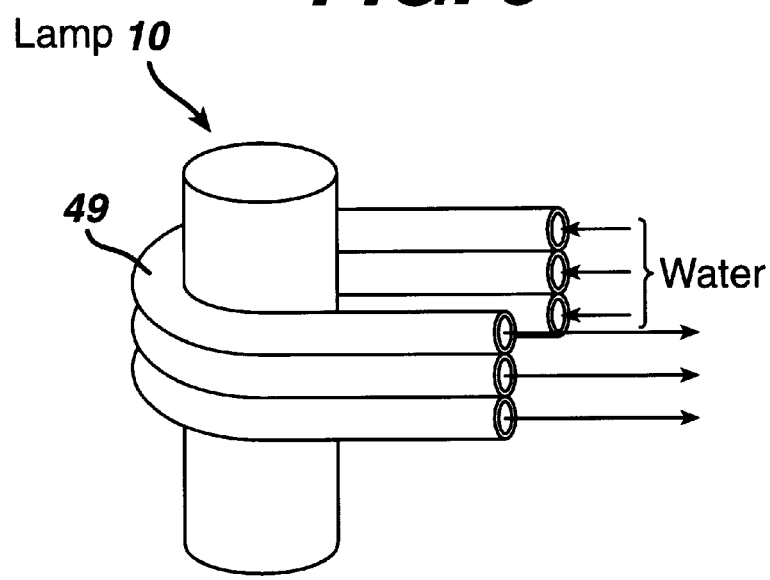
FIG. 6 is a perspective drawing of an embodiment of the invention having the flow of water split into three parallel channels each looped once around the lamp in a concentric loop configuration.

Envelope 17 may comprise a housing (e.g., cylindrical, as shown in FIG. 1) configured to have the water flow over the circumference of the lamp 10, as shown in FIG. 2. This means that, for this example, the path length that the bacteria would flow over is $\pi \times 50$ mm=15.7 cm. Alternative configurations are also workable, as illustrated in FIGS. 5 and 6. For example, a housing 48 about envelope 17 may comprise a single quartz tube wrapped several complete turns around the circumference of the lamp 10 (as shown in FIG. 5). Or individual quartz tubes 49 can be wrapped as single turns around the lamp 10 and placed adjacent to one another (as shown in FIG. 6) so that the water flow is split among the single turn tubes. For the example herein, the directly available UV flux, $\Gamma$, is 0.17W/cm$^2$ which is equivalent to 170,000$\mu$W/cm$^2$. This means that if it took 1 second for a microbe, bacteria or virus to traverse the path length (i.e. exposure time is 1 second), then the UV dosage as computed by $\Gamma \times$Exposure Time=170,000$\mu$W-sec/cm$^2$.

Figure 3:
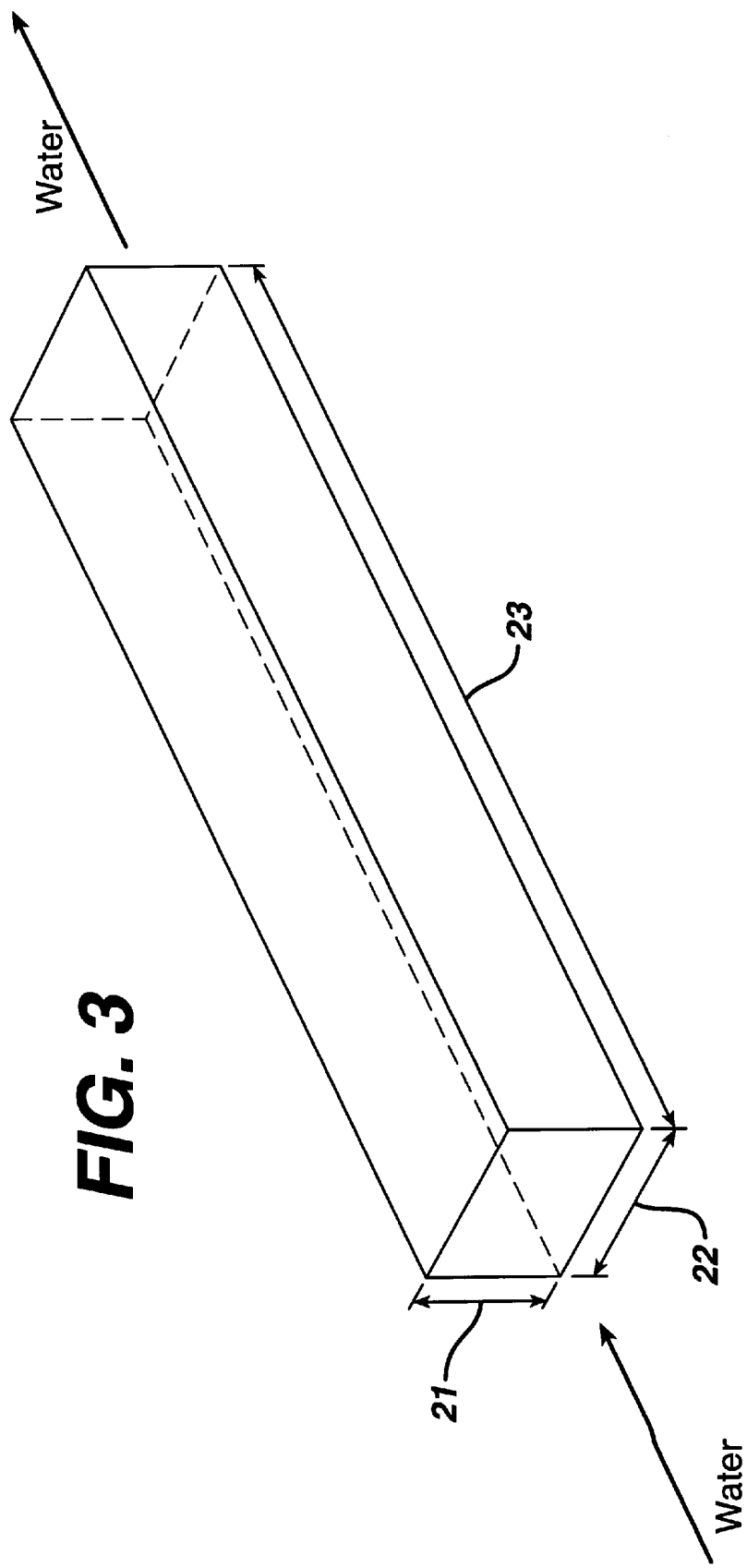
FIG. 3 illustrates the effective volume around the lamp of FIG. 1 exposed to ultraviolet radiation.

FIG. 3 illustrates an effective volume of water exposed to UV radiation by an electrodeless fluorescent lamp such as that of FIG. 1. The volume is illustrated as having a rectangular box shape. For example, for a width 22 of about 3 cm, approximately the size of the major axis discharge band, and a height 21 of about 3 cm, then the volume of water that flows in 1 second is 3 cm×3 cm×15.7 cm =141.30 cm², which is a flow rate of 0.141 liters per second. This is equivalent to 0.141×15.85032=2.23 gallons per minute. The additional 3 cm height gives an effective overall outside diameter (OD) of the lamp plus flow hardware of about 11 cm.

Throughput is a function of the dimensional constraints of a particular application. Increasing height 21 increases throughput. Similarly, if the overall OD of the system is increased, then throughput increases. Advantageously, the technology described is scalable and supports proportionally larger devices. Compactness of design and throughput are factors to be optimized depending on a particular application. To achieve compact design with high power, for example, a lamp with an OD in the range of 70 mm to 90 mm may be used such that the corresponding major and minor axes of the discharge toroid would be in the range of 20 mm to 25 mm and in the range of 10 mm to 15 mm, respectively.

Figure 4:
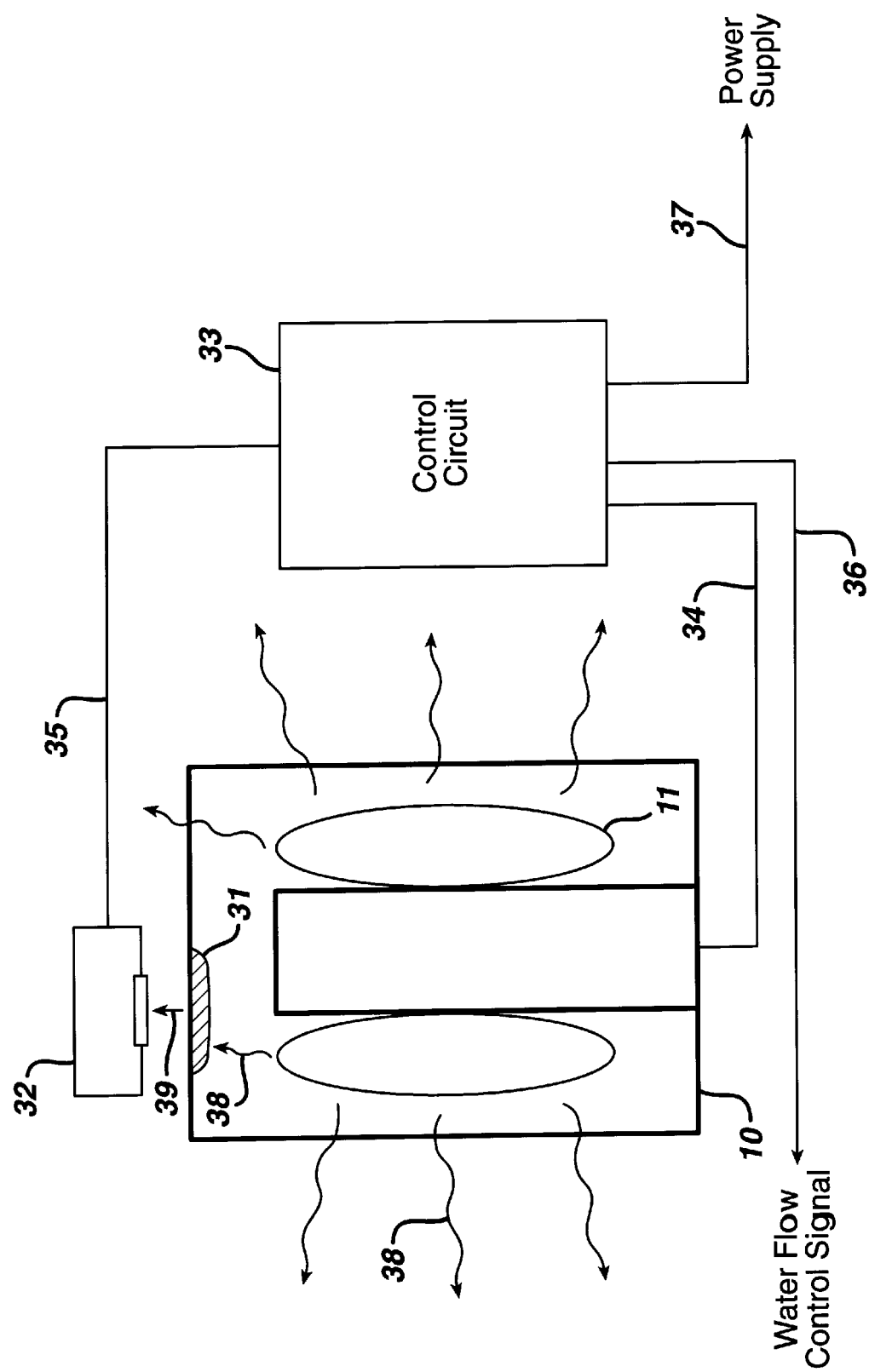
FIG. 4 illustrates a phosphor coating on a portion of the lamp, together with a photocell for detecting visible light and a circuit for controlling the flow of water around the lamp and for controlling power to the lamp.

FIG. 4 shows a phosphor 31 applied to at least a portion of the lamp envelope which is exposed to low amounts of UV radiation 38. Visible light 39 is generated when phosphor 31 is exposed to UV radiation 38. This visible light 39 is detected by photocell 32, the output 35 of which is directly proportional to the UV applied to the phosphor. As an alternative to phosphor 31, photocell 32 may be used for directly detecting UV radiation 38 such that a phosphor is not needed. A photocell output signal 35 is used by control circuit 33 for the following reasons: a) to send a signal 36 to control the water flow so that a desired UV dosage (represented by UV photons 38) is achieved; and b) to send a signal 37 to turn off the power connected to the lamp 10, for example, when the visible light 39 emitted by the phosphor 31 drops below a certain threshold value. Control circuitry used in this fashion would also prevent destruction of the lamp should ignition fail to occur during startup.

Lamps constructed according to preferred embodiments of the present invention have quartz envelopes (rather than glass which is usually used for lamps having electrodes), such as, for example, quartz known commercially as GE 214 quartz of General Electric Company, thereby enabling operation at higher power without damaging the envelopes.

While preferred embodiments of the invention have been described herein, those skilled in the art will recognize that such embodiments have been provided by way of example only. Numerous variations, changes and substitutions will occur to those of skill in the are without departing from the invention herein. Accordingly, it is intended that the invention be limited only by the spirit and scope of the appended claims.

What is claimed is:

1. An apparatus for disinfecting water using ultraviolet radiation, comprising:

a low pressure electrodeless discharge lamp having an envelope containing an ionizable, gaseous fill for sustaining an arc discharge when subjected to an alternating frequency magnetic field and for emitting ultraviolet radiation as a result thereof, the lamp having an excitation coil situated within the envelope for providing the alternating frequency magnetic field when excited by an alternating current power supply such that the discharge has a toroidal shape;

a housing for directing a flow of air around the lamp and through UV radiation emitted by the discharge; and a control circuit for controlling water flow rate and power to the lamp, the control circuit being responsive to UV radiation from the discharge.

2. The apparatus of claim 1 wherein the housing is cylindrical.

3. The apparatus of claim 1 wherein the lamp has an outside diameter of between 70 mm and 90 mm, a major axis of the toroidal discharge is between 20 mm and 25 mm, and a minor axis of the toroidal discharge is between 10 mm and 15 mm.

4. The apparatus of claim 1 wherein water flows around the lamp at a rate less than or equal to 2 gallons per minute.

5. The apparatus of claim 1 wherein the housing comprises a single tube wrapped a single turn around the lamp.

6. The apparatus of claim 1 wherein the housing comprises a single tube wrapped a plurality of turns around the lamp.

7. The apparatus of claim 1 wherein the housing comprises a plurality of parallel channels for water flow therethrough.

8. The apparatus of claim 1 wherein the control circuit comprises a photocell for detecting visible light emitted by a phosphor applied on at least a portion of the interior surface of the envelope, visible light emissions being triggered by the UV radiation striking the phosphor.

9. The apparatus of claim 1 wherein the control circuit comprises a photocell for directly detecting UV radiation from the lamp.

\* \* \* \* \*